US008068995B2

(12) United States Patent
Chau et al.

(10) Patent No.: US 8,068,995 B2
(45) Date of Patent: Nov. 29, 2011

(54) BIOSENSING APPARATUS AND SYSTEM (75) Inventors: Lai-Kwan Chau, Chiayi (TW);
Wen-Hsin Hsieh, Taipei (TW);
Wei-Ting Hsu, Taipei County (TW)

(73) Assignee: National Chung Cheng University, Chia-Yi (TW)

( * ) Notice: Subject to any disclaimer, the term of this patent is extended or adjusted under 35 U.S.C. 154(b) by 407 days.

(21) Appl. No.: 12/353,635

(22) Filed: Jan. 14, 2009

(65) Prior Publication Data
US 2009/0187350 A1 Jul. 23, 2009

Related U.S. Application Data

(60) Provisional application No. 61/011,527, filed on Jan. 18, 2008.

(51) Int. Cl.
| | |
|---|---|
| G02B 5/18 | (2006.01) |
| G02B 5/00 | (2006.01) |
| G02B 1/10 | (2006.01) |
| G02B 1/00 | (2006.01) |
| G02F 1/01 | (2006.01) |

(52) U.S. Cl. ............ 702/19; 356/38; 356/336; 356/337; 702/22; 977/701; 977/834; 977/932

(58) Field of Classification Search .................. 73/19.01, 73/23.2, 31.05, 31.06, 432.1, 865.8, 866; 261/1; 324/71.1, 71.5; 356/36, 38, 72, 300, 356/335, 336, 337, 432; 378/70, 71, 79, 378/82, 83, 86; 436/2, 43; 702/1, 19, 22, 702/27, 28, 30, 127, 187, 189; 977/700, 977/701, 832, 834, 902, 932
See application file for complete search history.

(56) References Cited

U.S. PATENT DOCUMENTS

| | | | | | |
|---|---|---|---|---|---|
| 4,810,658 | A | * | 3/1989 | Shanks et al. | 436/172 |
| 5,017,009 | A | * | 5/1991 | Schutt et al. | 356/338 |
| 5,341,215 | A | * | 8/1994 | Seher | 356/445 |
| 5,350,697 | A | * | 9/1994 | Swope et al. | 436/527 |
| 5,455,178 | A | * | 10/1995 | Fattinger | 436/164 |

(Continued)

OTHER PUBLICATIONS

Hsu et al: [P3.16] "Label-free biosensor based on localized plasmon resonance coupled with diffraction", The Tenth World Congress on Biosensors, Delegate Manual, Shanghai, China, May 14-16, 2008, (Abstract Only).*

(Continued)

Primary Examiner — Edward Cosimano
(74) Attorney, Agent, or Firm — WPAT, P.C.; Anthony King (57) ABSTRACT

A bio-sensing system comprises a light source, a bio-sensing apparatus, a detecting platform, and a processing unit. A bio-sensing apparatus further comprising a substrate, a sample with at least one analyte, at least one grating bound on the substrate for diffracting a light beam in a reflection mode and outputting at least one output light beam, a plurality of nanoparticles being bound on one side of the grating, a molecular recognition unit bound on said nanoparticle surface, and a cover plate covering the nanoparticle-modified side of the substrate. The detecting platform receives a signal while the at least one output light beam passing through the bio-sensing apparatus. The processing unit couples with the detecting platform for receiving and analyzing the signal. Wherein when the analyte passes through the microfludic channel to contact with said nanoparticles, the at least one output light beam changes in accordance with the refractive index of the sample or in accordance with the interaction of the analyte with said molecular recognition unit bound on said nanoparticle surface.

28 Claims, 9 Drawing Sheets

U.S. PATENT DOCUMENTS

| | | | | |
|---|---|---|---|---|
| 5,515,163 | A * | 5/1996 | Kupershmidt et al. | 356/338 |
| 5,629,213 | A * | 5/1997 | Kornguth et al. | 436/518 |
| 5,875,032 | A * | 2/1999 | Naya | 356/445 |
| 5,991,488 | A | 11/1999 | Salamon et al. | 385/129 |
| 6,330,387 | B1 * | 12/2001 | Salamon et al. | 385/129 |
| 6,421,128 | B1 * | 7/2002 | Salamon et al. | 356/445 |
| 6,577,396 | B1 * | 6/2003 | Naya | 356/445 |
| 6,833,542 | B2 * | 12/2004 | Wang et al. | 250/251 |
| 6,970,249 | B1 * | 11/2005 | Lipson et al. | 356/445 |
| 7,110,585 | B2 * | 9/2006 | Cork et al. | 382/128 |
| 7,314,749 | B2 * | 1/2008 | Goh et al. | 435/287.1 |
| 7,407,817 | B2 * | 8/2008 | Ho et al. | 436/524 |
| 7,420,682 | B2 * | 9/2008 | Salamon et al. | 356/445 |
| 7,511,820 | B2 * | 3/2009 | Chau et al. | 356/445 |
| 7,892,855 | B2 * | 2/2011 | Ho et al. | 436/525 |
| 2002/0132316 | A1 * | 9/2002 | Wang et al. | 435/173.9 |
| 2003/0049693 | A1 * | 3/2003 | Goh et al. | 435/7.9 |
| 2003/0068638 | A1 * | 4/2003 | Cork et al. | 435/6 |
| 2005/0053974 | A1 * | 3/2005 | Lakowicz et al. | 435/6 |
| 2006/0197952 | A1 * | 9/2006 | Chen et al. | 356/445 |
| 2007/0030489 | A1 * | 2/2007 | Salamon et al. | 356/451 |
| 2007/0109544 | A1 * | 5/2007 | Chau et al. | 356/445 |
| 2007/0109545 | A1 * | 5/2007 | Chau et al. | 356/445 |
| 2007/0166763 | A1 * | 7/2007 | Ho et al. | 435/7.1 |
| 2009/0086210 | A1 * | 4/2009 | Ho et al. | 356/445 |

OTHER PUBLICATIONS

Hsu et al: "A Label-Free Biosensor using gold nanoparticles-modified diffraction grating", International Chemical Conference, Taipei: Analytical Chemistry, National Sun Yat-Sen University, Kaohsiun, Taiwan, Oct. 2-5, 2008, p. 104 (Abstract Only).*

* cited by examiner

BIOSENSING APPARATUS AND SYSTEM

This application claims priority to expired Provisional Patent Application No. 61/011,527, filed on Jan. 18, 2008, the entire contents of all of which are hereby incorporated by reference.

FIELD

The exemplary embodiment(s) of the present invention relates to a field of a bio-sensing apparatus and a system. More specifically, the exemplary embodiment(s) of the present invention relates to a bio-sensing apparatus and a system using localized plasmon resonance coupled with diffraction.

BACKGROUND

Since surface plasmon resonance (SPR) spectroscopy is in widespread use for probing interfacial phenomena according to measurement of minute changes in charge density wave of free electrons within a metal film, the experimental configuration for SPR sensing can be applied to a thin noble metal film and the flat surface of a prism in which polarized light of a single wavelength is introduced at an angle, so that internal reflectance is achieved. It plays an important role of probing interaction between molecules and also provides label-free bio-sensing for probing the affinity between biological molecules. However, a standard SPR biosensor is designed according to the measurement and recording of the reflected light, and a shift in the angle of the incident beam corresponding to optimal surface plasmon coupled with the metal film is generated. Consequently, the foregoing optical setup is expensive, inconvenience and difficult to be miniaturized.

SUMMARY

A bio-sensing apparatus and a system using localized plasmon resonance coupled with diffraction is disclosed. A primary object of the present invention is to provide a bio-sensing apparatus comprises a substrate, a sample, at least one grating, a plurality of nanoparticles, a molecular recognition unit functionalized on said nanoparticle surface, and a cover plate. The sample comprises at least one analyte. A plurality of nanoparticles is bound on the same side of the grating or the other side of the grating. The cover plate covers the nanoparticles. Wherein at least one output light beam changes in accordance with the refractive index of the sample or in accordance with interaction of an analyte with the molecular recognition unit bound on the nanoparticle surface.

Another object of the present invention is to provide a bio-sensing system comprises a light source, a bio-sensing apparatus, a detecting platform, and a processing unit. The bio-sensing apparatus comprises a substrate, a sample, at least one grating, a plurality of nanoparticles, a molecular recognition unit functionalized on said nanoparticle surface, and a cover plate. The substrate comprises at least one grating. The sample comprises at least one analyte. A plurality of nanoparticles is bound on the same side of the grating or the other side of the grating. A cover plate covers the nanoparticles. Wherein at least one output light beam changes in accordance with the refractive index of the sample or in accordance with interaction of an analyte with the molecular recognition unit bound on the nanoparticle surface. The detecting platform detects the diffraction angle or diffraction intensity of at least one light beam and transmits the information to the processing unit.

With these and other objects, advantages, and features of the invention that may become hereinafter apparent, the nature of the invention may be more clearly understood by reference to the detailed description of the invention, the embodiments and to the several drawings herein.

BRIEF DESCRIPTION OF THE DRAWINGS

The exemplary embodiment(s) of the present invention will be understood more fully from the detailed description given below and from the accompanying drawings of various embodiments of the invention, which, however, should not be taken to limit the invention to the specific embodiments, but are for explanation and understanding only.

DETAILED DESCRIPTION

Exemplary embodiments of the present invention are described herein in the context of a bio-sensing apparatus and a system using localized plasmon resonance coupled with diffraction.

Those of ordinary skilled in the art will realize that the following detailed description of the exemplary embodiment(s) is illustrative only and is not intended to be in any way limiting. Other embodiments will readily suggest themselves to such skilled persons having the benefit of this disclosure. Reference will now be made in detail to implementations of the exemplary embodiment(s) as illustrated in the accompanying drawings. The same reference indicators will be used throughout the drawings and the following detailed description to refer to the same or like parts.

An intrinsic resonance phenomenon of free electron waves in metal nanoparticles known as localized plasmon resonance (LPR) is considered as a technique. LPR defines the collective charge density oscillations of nanoparticles, and can be set without utilizing the attenuated total reflection (ATR) optical setup. Similar to conventional SPR based on ATR, the resonance condition can detect an immediate change in the interfacial refractive index (RI) of the surrounding medium as well as the bio-molecular interactions at the nanoparticle-solution interface. Therefore, very small sensors can be possibly made by using the LPR technique with a simple optical set up.

The LPR technique is applied to provide a highly sensitive label-free optical biosensor without any bulky optics. In the biosensor, gold nanoparticles are immobilized on a surface of a glass slide and in contact with a sample when a diffraction grating based on UV-assisted embossing, holography, or injection molding is disposed on a reverse surface of the slide. Using diffraction in reflection mode, signals such as the angle or intensity of the reflected/diffracted light beam can be monitored by a position-sensitive detector (PSD) or a light intensity detector, respectively. Such signals are highly sensitive to change in refractive index of the environment near the gold nanoparticles and biomolecular interactions at the surface of the gold nanoparticles. It should be noted that the nature of the nanoparticles is not limited to gold, and can be extended to other noble metal nanoparticles. The sensor can be easily fabricated and constructed by simple optical designs. Further, the sensor has the potential capability for on-site sensing and is disposable.

Figure 1A:
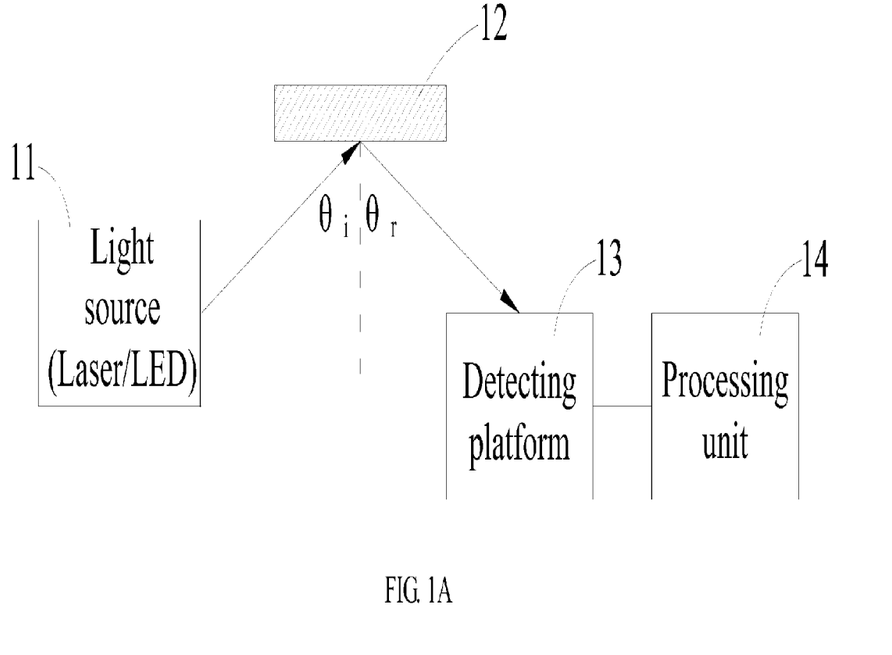
FIG. 1A illustrates an optical setup for the sensing system in accordance with one embodiment of the present invention.

Please refer to FIG. 1(A). FIG. 1(A) shows an optical setup for the sensing system. A light source 11 comprising of a laser emits a laser beam that is incident on the grating of the sensor apparatus 12 to excite the localized plasmon modes at an incident angle $\theta_i$. Alternatively, the light source 11 may also be a light emitted diode (LED). Since optimum performance is achieved by coupling of the laser beam into the glass slide, the incident angle is at a specific range. The grating then reflects/diffracts the laser beam that is measured by a detecting platform 13 at an angle $\theta_r$ to complete the entire apparatus. The detecting platform may be a position-sensitive detector (PSD) or a light intensity detector. The processing unit 14 calculates and displays the measurement results on display for user. Then the optical setup for the sensing system can be operated and completed.

Figure 1B:
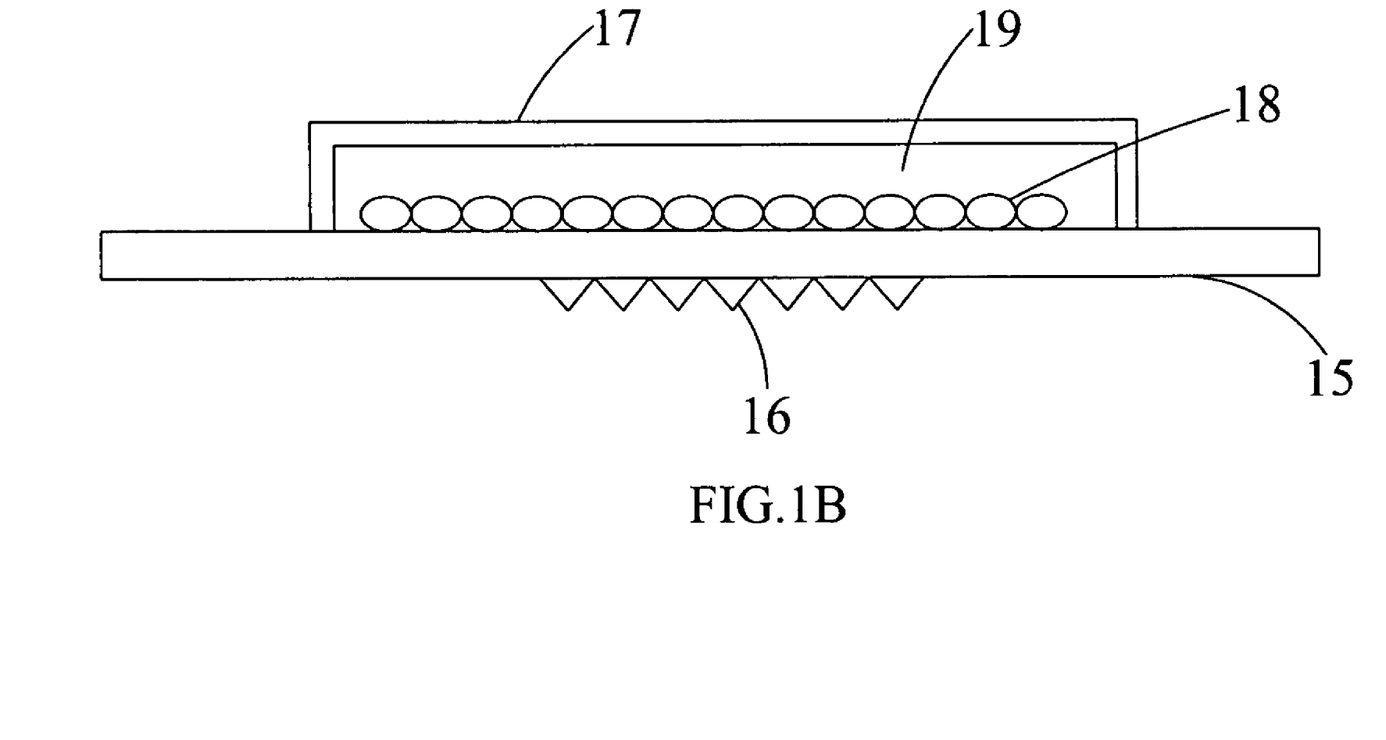
FIG. 1B illustrates a sensing apparatus of the structure in accordance with one embodiment of the present invention.

FIG. 1(B) illustrates a sensing apparatus of the structure in accordance with one embodiment of the present invention. The sensing apparatus reflects/diffracts a light beam and outputs at least one out light beam. The detecting platform detects the diffraction angle and/or the light intensity of at least one output light beam. A bio-sensing apparatus comprises a substrate 15, at least one grating 16, a cover plate 17, and a plurality of nanoparticles 18. The grating 16 is disposed on the substrate 15. A plurality of nanoparticles 18 is bound on another side of the grating 16. The substrate further functions as a waveguide layer. The sensing apparatus uses localized plasmon resonance coupled with diffraction. The cover plate 17 of the sensing apparatus with microfluid channel 19 covers a plurality of nanoparticles 18. Furthermore, the nanoparticles 18 may be further functionalized with a molecular recognition unit. The molecular recognition unit may be a chemoreceptor, an antibody, an antigen, a lectin, a hormone receptor, a nucleic acid, or a carbohydrate. The molecular recognition unit is capable of sensing a metal ion, an antibody, an antigen, a cytokine, a hormone, a growth factor, a neuropeptide, a hemoglobin, a plasma protein, an amino acid, a vitamin, a nucleic acid, a carbohydrate, a glycoprotein, a fatty acid, a phosphatidic acid, a sterol, an antibiotic, a cell, a toxin, a virus, or a bacterium. For example, the chelating ability of some chemical molecules is capable of sensing some carbohydrates or some metal ions. An antibody probe is capable of sensing the corresponding antigen. An antigen probe is capable of sensing the corresponding antibody. A deoxyrinonucleic acid probe is capable of sensing the complementary deoxyrinonucleic acid. A carbohydrate probe is capable of sensing a bacterium with a recognizable epitope and so on.

To prepare the structure of the sensor apparatus, a substrate is submerged into a vial of solution of 3-(mercapropyl)-trimethoxysilane (MPTMS) in toluene. The modified substrate is then immersed in a solution having gold nanoparticles to form a self-assembled gold nanoparticle monolayer on the surface of the substrate. A cover plate 17 made of poly(methyl methacrylate) (PMMA) with a microfludic channel 19 is bound on the gold nanoparticle-modified side of the substrate. The grating fabricated by UV-assisted embossing is also disposed on the reverse side of the substrate to have a good performance with sensing apparatus.

Figure 1C:
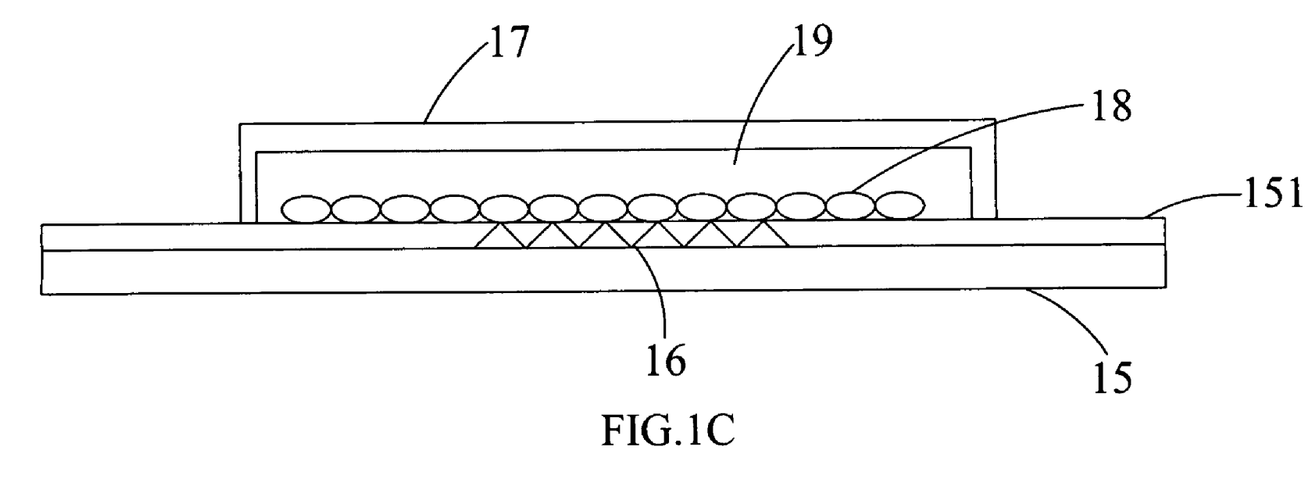
FIG. 1C illustrates a sensing apparatus of the structure in accordance with another embodiment of the present invention.

FIG. 1(C) illustrates a sensing apparatus of the structure in accordance with another embodiment of the present invention. The planar waveguide 151 prepared by sol-gel process, sputtering, or photopolymerization is coated over the substrate 15, and the grating 16 is directly disposed within the planar waveguide 151. Noble metal nanoparticles 18 are immobilized on the surface of the grating. A cover plate 17 with a microfludic channel 19 is bound on the nanoparticle-modified side of the chip. The substrate 15 may be a glass substrate or a polymer thin film substrate. The nanoparticles 18 may be noble metal nanoparticles of different sizes and/or shapes. The grating 16 may be a diffraction grating.

Figure 2A:
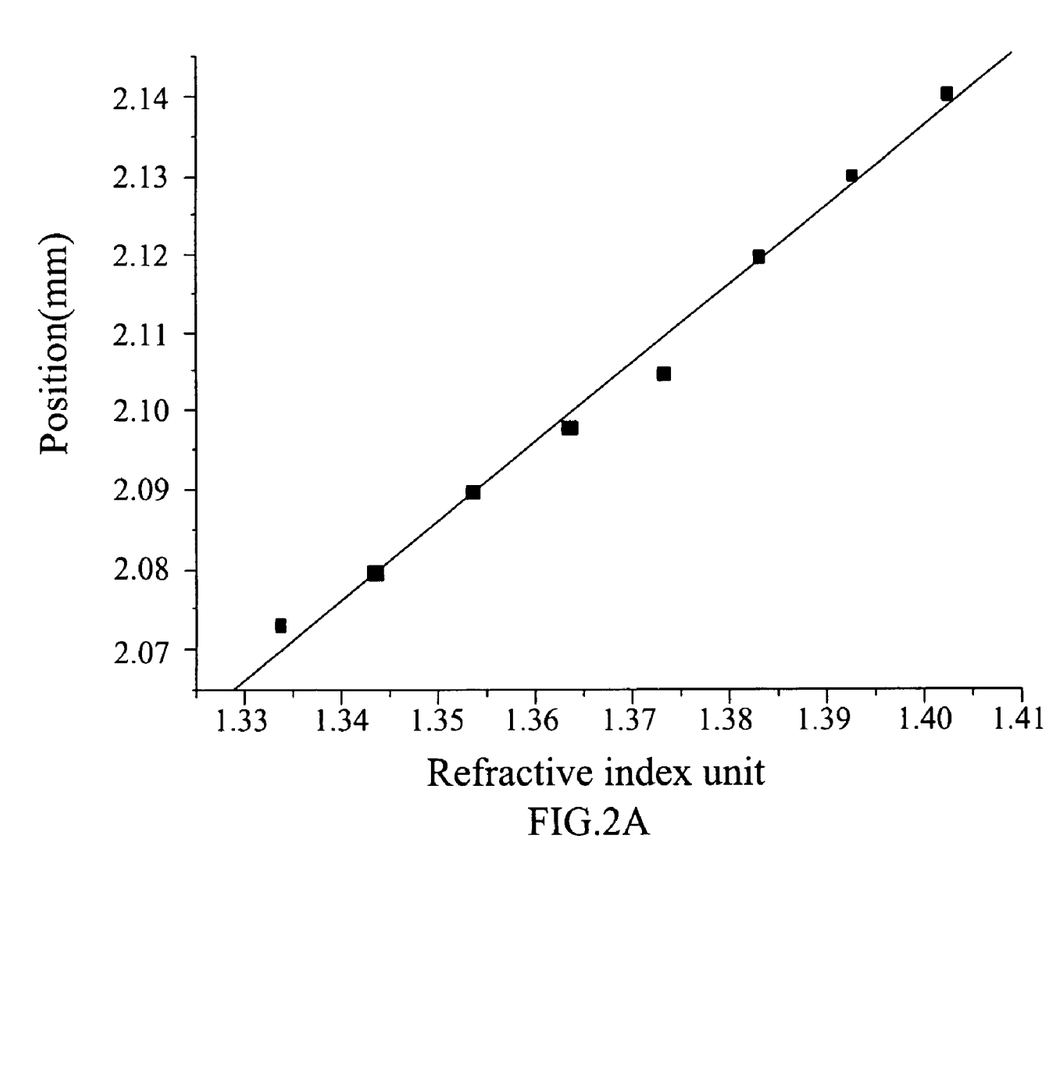
FIG. 2A shows a plot of the position of a sensing system versus refractive index of sucrose solution in accordance with one embodiment of the present invention.
Figure 2B:
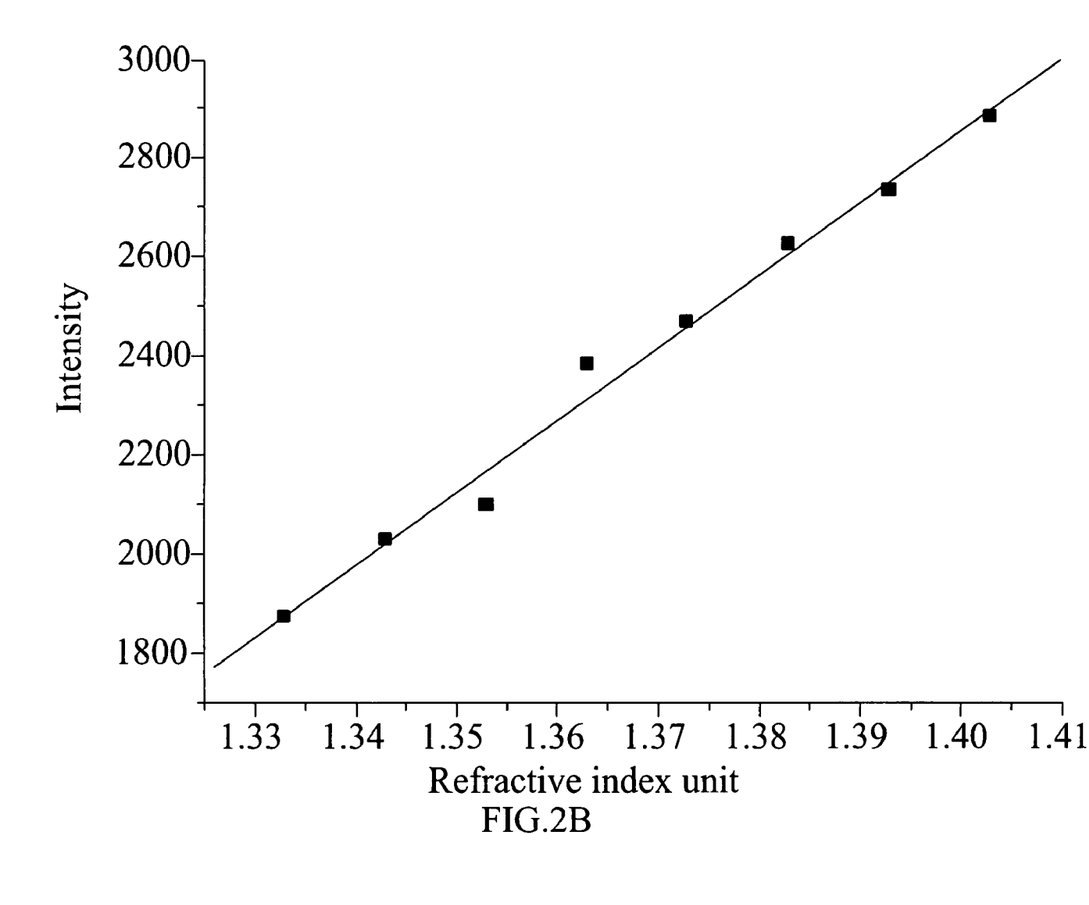
FIG. 2B shows a plot of the intensity of a sensing system versus refractive index of sucrose solution in accordance with one embodiment of the present invention.

FIG. 2A shows a plot of the position of a sensing system versus refractive index of sucrose solution in accordance with one embodiment of the present invention. The detecting platform 13 measures the position of the reflected/diffracted light beam by exposing the bare gold nanaoparticle surface in sucrose solutions of various refractive indexes. The detecting platform 13 may be a position-sensitive detector (PSD) or a light intensity detector. When the refractive index of the sucrose solution is increased, the position of the reflected/diffracted light beam at PSD shifts linearly versus refractive index of the solution as shown in FIG. 2A. The plot of the intensity of the reflected/diffracted light beam at PSD versus refractive index also has a linear relation as shown in FIG. 2B.

Figure 3:
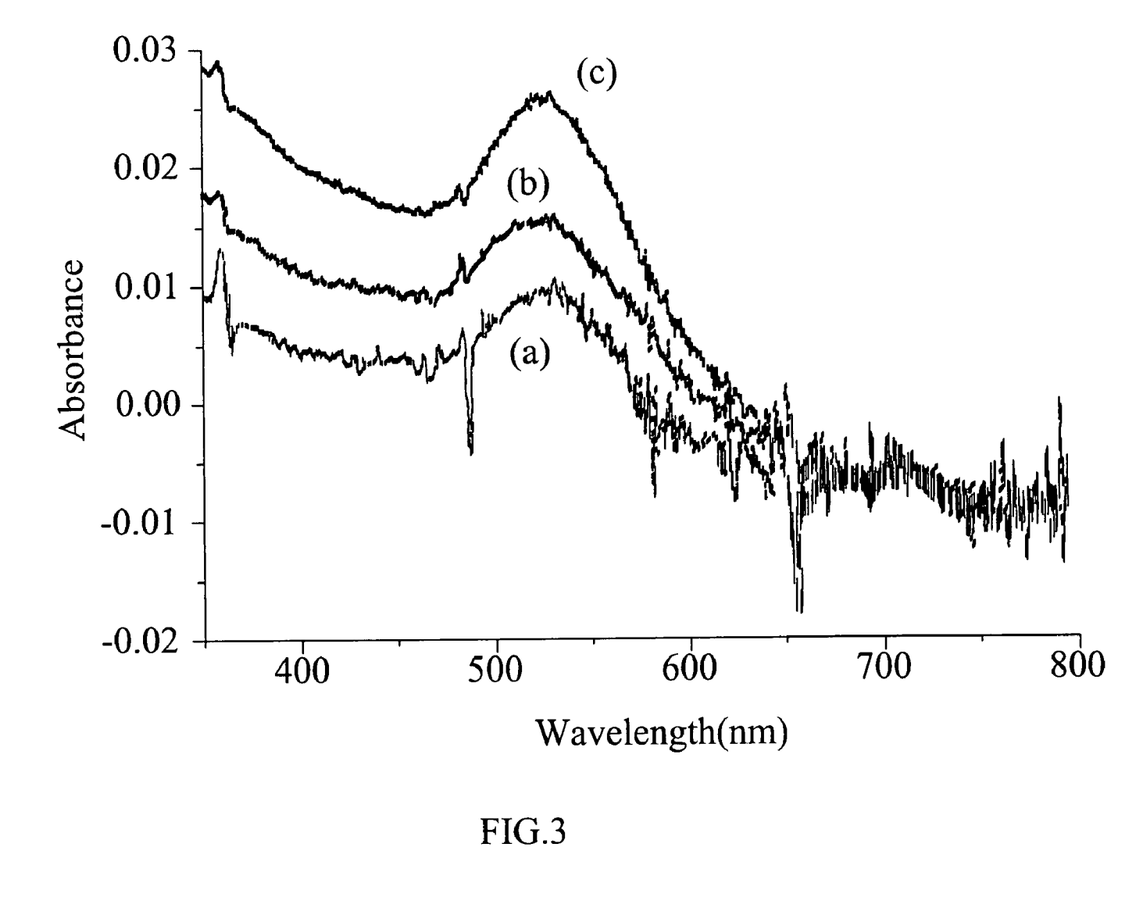
FIG. 3 is the absorbance spectra of a sensing system in accordance with one embodiment of the present invention.

FIG. 3 is the absorbance spectra of a sensing system in accordance with one embodiment of the present invention. As shown, curves (a), (b) and (c) are the absorbance spectra of the unmodified gold nanoparticles, the gold nanoparticles modified with DNP (dinitrophenyl antigen), and the gold nanoparticles with DNP binding with anti-DNP, respectively. The shifts in peak wavelength and increases in peak absorbance are observed after modification of the gold nanoparticle surface with DNP (dinitrophenyl antigen) and after further binding with anti-DNP. Such spectral changes are consistent with the fact that the extinction spectra of gold nanoparticles are sensitive to the refractive index of the surrounding environment.

Figure 4:
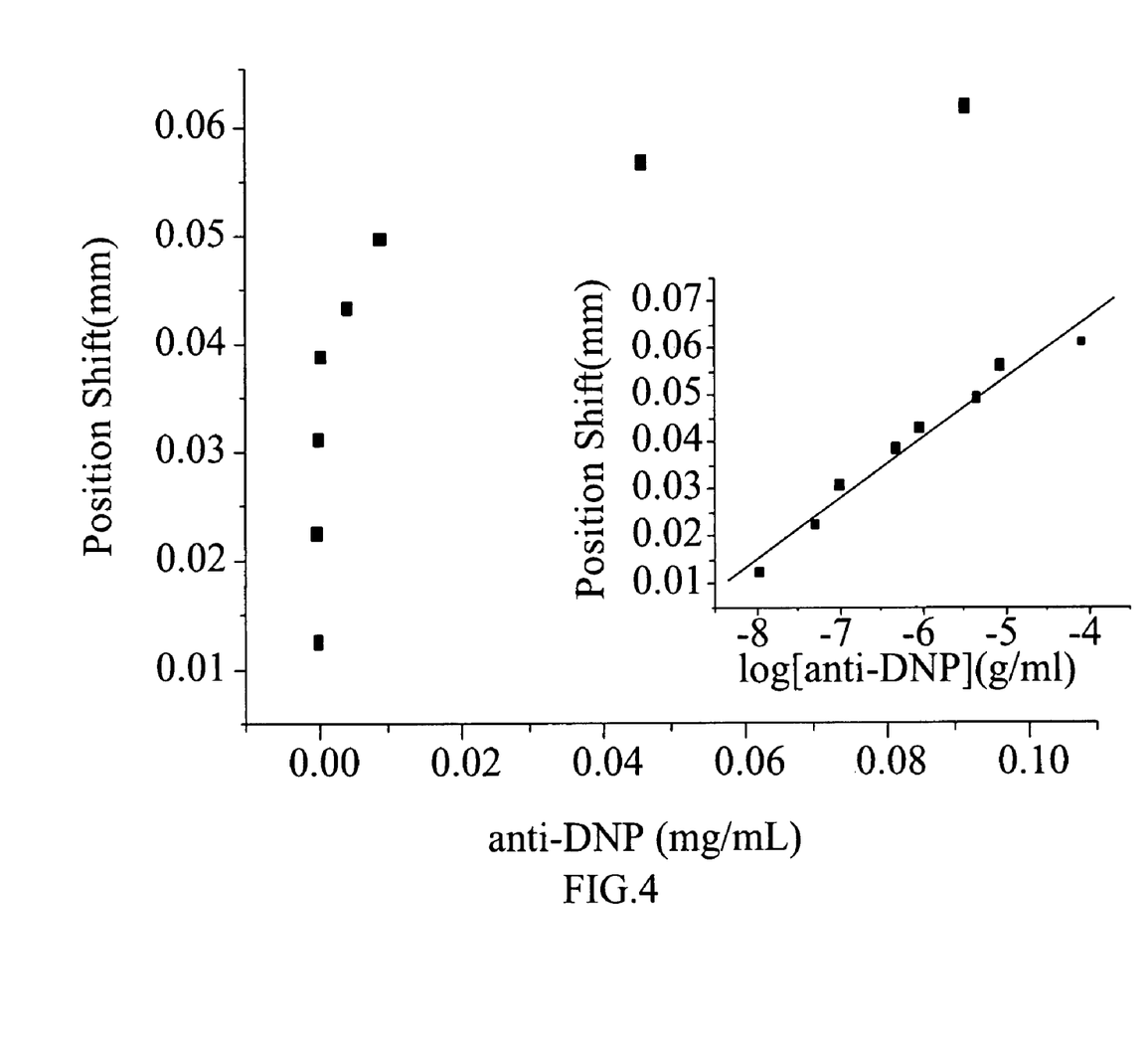
FIG. 4 is a plot of the position shift versus anti-DNP concentration. Inset: The sensor response versus-log(anti-DNP concentration)

FIG. 4 shows a plot of the position shift versus anti-DNP concentration. FIG. 4 shows the calibration graph of the equilibrium sensor responses (position shifts) corresponding to anti-DNP concentrations. Over the concentration range, the plot of the sensor response versus-log concentration of anti-DNP is linear as shown in the inset of FIG. 4. Immediate interactive information on the sample can be obtained through real-time detection. The concentration-dependent response of the sensor is monitored in real-time by monitoring the position shift of the reflected/diffracted light beam at PSD.

Figure 5:
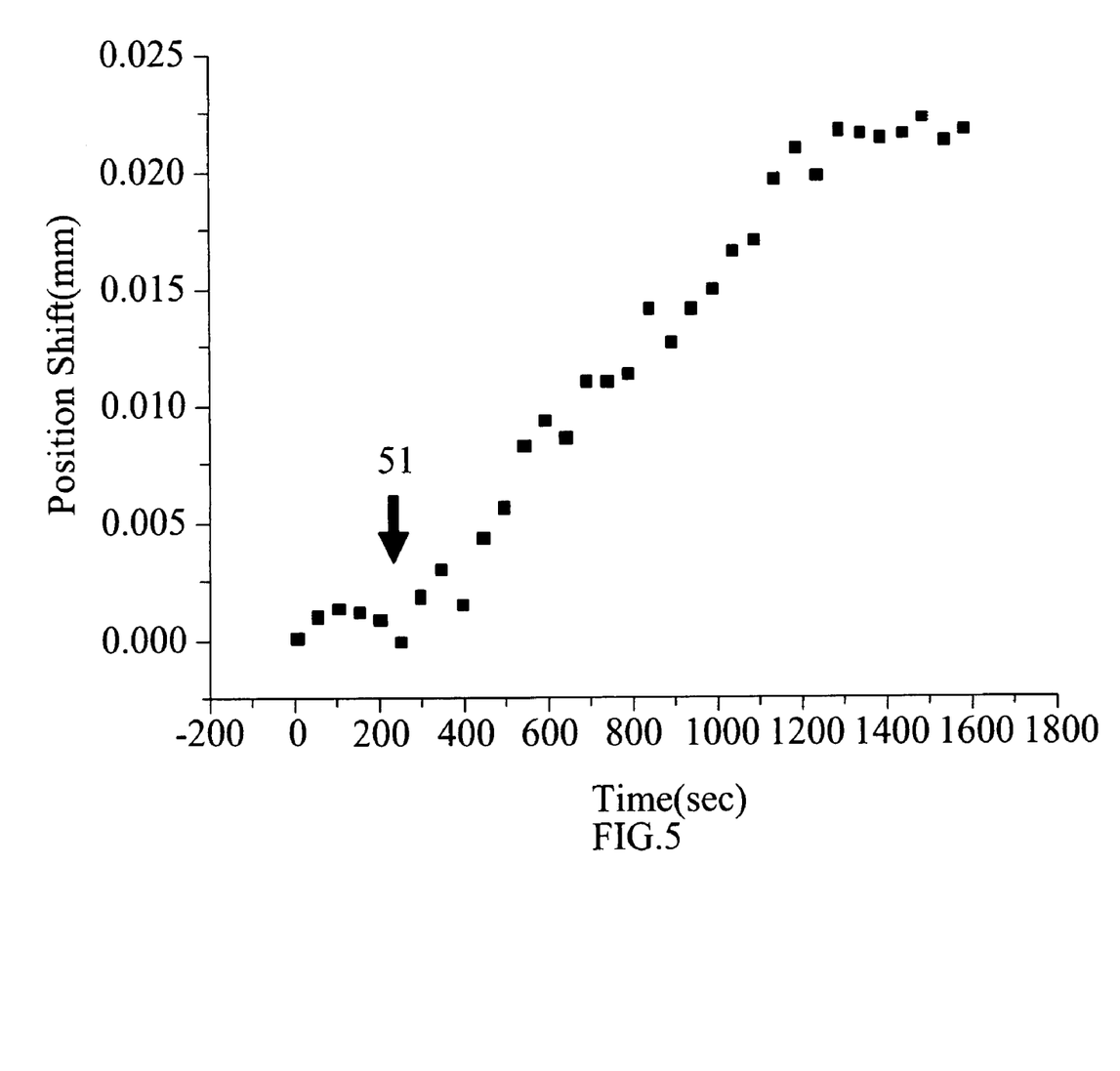
FIG. 5 is the temporal response of a sensor apparatus versus the position shift in accordance with one embodiment of the present invention.
Figure 6:
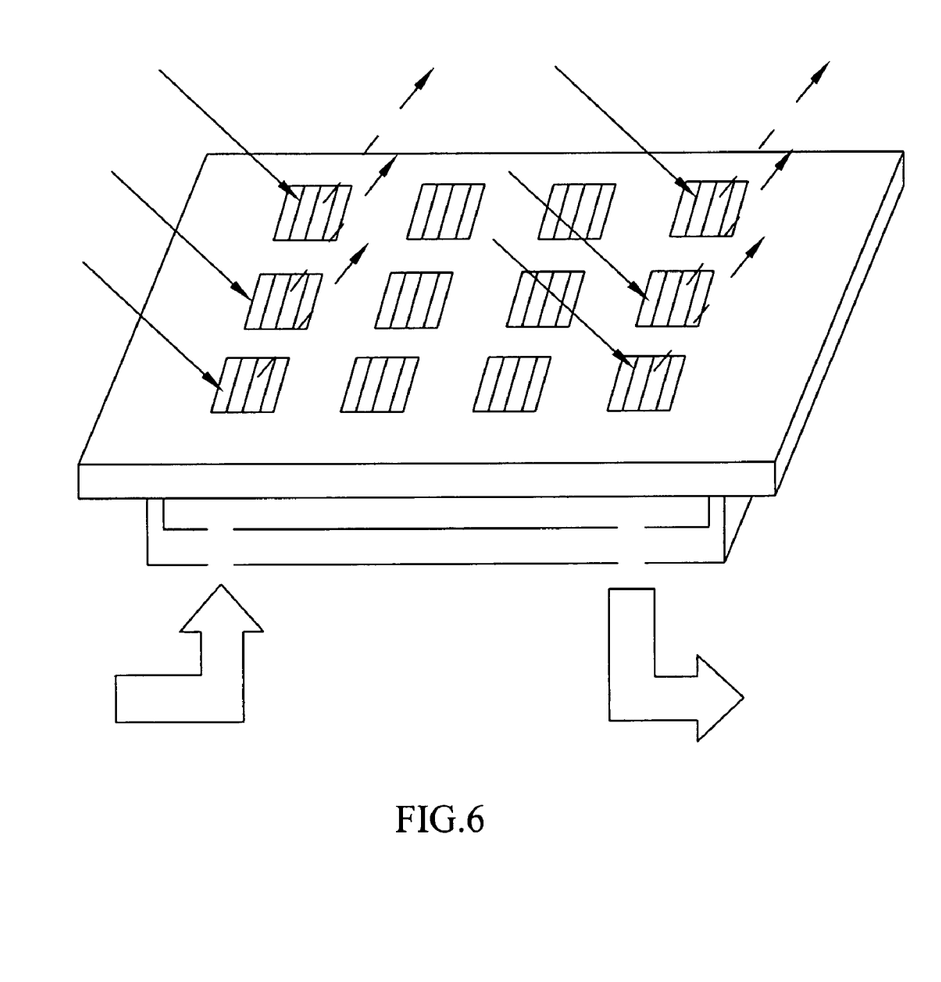
FIG. 6 is an array format of the sensing apparatus in accordance with one embodiment of the present invention.

FIG. 5 is the temporal response of a sensor apparatus versus the position shift in accordance with one embodiment of the present invention. A clear response showing the affinity between DNP and anti-DNP is therefore observed. Upon injection of the anti-DNP solution (illustrated by arrow 51), the sensor response changed drastically and a steady-state sensor response is observed after about 900 s. According to the experimental results of FIGS. 2A, 2B, 3, 4 and 5, the sensing apparatus 12 has a high sensing ability by which the output light beam changes in accordance with refractive index of the sample or in accordance with interaction of an analyte with a molecular recognition unit bound on the nanoparticle surface. The detecting platform then detects the intensity or position of the reflected/diffracted light beam. FIG. 6 is an array format of the sensing apparatus in accordance with one embodiment of the present invention. Further, multiplex detection can be achieved through an array format composed of fabricating a plurality of gratings.

Accordingly, the high sensitivity of the bio-sensing apparatus with respect to analyte concentration represents an approach to bio-interaction analysis that utilizes a very simple and cost-effective optical setup with disposable chips. The sensing system comprises a light source, a sensing apparatus, a detecting platform, and a processing unit (With refer to FIG. 1A). The sensing apparatus is also label-free, rapid, and requires small sample volume. The bio-sensing apparatus has the potential of scaling a laser spot down without losing sensitivity and is amenable to integration with micro-fluidics for high-throughput determinations.

While particular embodiments of the present invention have been shown and described, it will be obvious to those skilled in the art that, based upon the teachings herein, changes and modifications may be made without departing from this invention and its broader aspects. Therefore, the appended claims are intended to encompass within their scope of all such changes and modifications as are within the true spirit and scope of the exemplary embodiment(s) of the present invention.

What is claimed is:

1. A bio-sensing apparatus, comprising:
   a substrate;
   at least one grating being bound on said substrate for diffracting a light beam in a reflection mode and outputting at least one output light beam;
   a plurality of nanoparticles being bound on one side of said grating; and
   a cover plate comprising a microfluid channel for accommodating a sample with at least one analyte;
   wherein said at least one output light beam changes in accordance with refractive index of said sample or in accordance with interaction of said analyte with said nanoparticles.

2. The bio-sensing apparatus of claim 1, wherein said substrate is a glass substrate or a polymer thin film substrate.

3. The bio-sensing apparatus of claim 1, wherein said nanoparticles are noble metal nanoparticles.

4. The bio-sensing apparatus of claim 1, wherein said nanoparticles are made of gold nanoparticles or silver nanoparticles.

5. The bio-sensing apparatus of claim 1, wherein said grating is a diffraction grating.

6. The bio-sensing apparatus of claim 1, wherein said nanoparticles are disposed on the same side or the other side of said grating.

7. The bio-sensing apparatus of claim 1, wherein said cover plate covers said nanoparticles.

8. The bio-sensing apparatus of claim 1, wherein said substrate further comprises a waveguide layer.

9. The bio-sensing apparatus of claim 8, wherein said waveguide layer is made by sol-gel process, sputter deposition, or photopolymerization.

10. The bio-sensing apparatus of claim 1, wherein said nanoparticles are further functionalized with a molecular recognition unit for sensing a specific kind of molecules.

11. The bio-sensing apparatus of claim 10, wherein said molecular recognition unit is a chemoreceptor, an antibody, an antigen, a lectin, a hormone receptor, a nucleic acid, or a carbohydrate.

12. The bio-sensing apparatus of claim 11, wherein said molecular recognition unit is for sensing a metal ion, an antibody, an antigen, a cytokine, a hormone, a growth factor, a neuropeptide, a hemoglobin, a plasma protein, an amino acid, a vitamin, a nucleic acid, a carbohydrate, a glycoprotein, a fatty acid, a phosphatidic acid, a sterol, an antibiotic, a cell, a toxin, a virus, or a bacterium.

13. A bio-sensing system, comprising:
   a light source providing a light beam;
   a bio-sensing apparatus, comprising:
      a substrate;
      at least one grating being bound on said substrate for diffracting a light beam in a reflection mode and outputting at least one output light beam;
      a plurality of nanoparticles being bound on one side of said grating; and
      a cover plate comprising a microfluid channel for accommodating a sample with at least one analyte;
   a detecting platform receiving a signal while said at least one output light beam passing through said bio-sensing apparatus; and
   a processing unit coupling with said detecting platform for receiving and analyzing said signal;
   wherein said at least one output light beam changes in accordance with refractive index of said sample or in accordance with interaction of said analyte with said nanoparticles.

14. The bio-sensing system of claim 13, wherein said substrate is a glass substrate or a polymer thin film substrate.

15. The bio-sensing system of claim 13, wherein said nanoparticles are noble metal nanoparticles.

16. The bio-sensing system of claim 13, wherein said nanoparticles are made of gold nanoparticles or silver nanoparticles.

17. The bio-sensing system of claim 13, wherein said detecting platform is a position-sensitive detector (PSD) or a light intensity detector.

18. The bio-sensing system of claim 13, wherein said grating is a diffraction grating.

19. The bio-sensing system of claim 13, wherein said nanoparticles are disposed on the same side or the other side of said grating.

20. The bio-sensing system of claim 13, wherein said cover plate covers said nanoparticles.

21. The bio-sensing system of claim 13, wherein said detecting platform detects diffraction angle or intensity of said at least one output light beam.

22. The bio-sensing system of claim 13, wherein said light source is a laser or a Light Emitted diode (LED).

23. The bio-sensing system of claim 13, wherein said processing unit is a computer unit.

24. The bio-sensing system of claim 13, wherein said substrate further comprises a waveguide layer.

25. The bio-sensing system of claim 24, wherein said waveguide layer is made by sol-gel process, sputter deposition, or photopolymerization.

26. The bio-sensing system of claim 13 wherein said nanoparticles are further functionalized with a molecular recognition unit for sensing a specific kind of molecules.

27. The bio-sensing system of claim 26, wherein said molecular recognition unit is a chemoreceptor, an antibody, an antigen, a lectin, a hormone receptor, a nucleic acid, or a carbohydrate.

28. The bio-sensing system of claim 27, wherein said molecular recognition unit is for sensing a metal ion, an antibody, an antigen, a cytokine, a hormone, a growth factor, a neuropeptide, a hemoglobin, a plasma protein, an amino acid, a vitamin, a nucleic acid, a carbohydrate, a glycoprotein, a fatty acid, a phosphatidic acid, a sterol, an antibiotic, a cell, a toxin, a virus, or a bacterium.

* * * * *